United States Patent [19]

Fujimori et al.

[11] Patent Number: 4,713,683

[45] Date of Patent: Dec. 15, 1987

[54] ILLUMINATING AND SYNCHRONIZING DEVICE FOR COLOR IMAGING EQUIPMENT

[75] Inventors: Hiroyoshi Fujimori, Hachioji; Tatsuo Nagasaki, Musashino, both of Japan

[73] Assignee: Olympus Optical Co., Ltd., Tokyo, Japan

[21] Appl. No.: 768,998

[22] Filed: Aug. 26, 1985

[30] Foreign Application Priority Data

Aug. 31, 1984 [JP]  Japan .................... 59-183085

[51] Int. Cl.$^4$ ............ H04N 9/04; H04N 7/18; A61B 1/06
[52] U.S. Cl. ........................ 358/42; 358/98; 118/6
[58] Field of Search ............ 358/42, 43, 98, 44; 128/4–6; 355/35; 362/293

[56] References Cited

U.S. PATENT DOCUMENTS

| 3,600,504 | 8/1971 | Reilly | 358/42 |
|---|---|---|---|
| 3,654,385 | 4/1972 | Flagle | 358/42 |
| 4,074,306 | 2/1978 | Kakinuma et al. | 358/98 |
| 4,253,447 | 3/1981 | Moore et al. | 128/6 |
| 4,423,436 | 12/1983 | Kimura | 358/98 |
| 4,532,918 | 8/1985 | Wheeler | 358/98 |
| 4,546,379 | 10/1985 | Sarofeen et al. | 358/42 |
| 4,593,313 | 6/1986 | Nagasaki et al. | 358/42 |
| 4,604,992 | 8/1986 | Sato | 358/98 |
| 4,631,582 | 12/1986 | Nagasaki et al. | 358/98 |

FOREIGN PATENT DOCUMENTS

| 65962 | 8/1976 | Japan . | |
| 55-123279 | 9/1980 | Japan . | |
| 58-43688 | 3/1983 | Japan | 358/42 |

*Primary Examiner*—James J. Groody
*Assistant Examiner*—Robert M. Bauer
*Attorney, Agent, or Firm*—Armstrong, Nikaido, Marmelstein & Kubovcik

[57] ABSTRACT

An illuminating device is provided to serve as a lighting source for a subject to be imaged by color imaging equipment and a source of synchronizing signals, and is adjustable to provide light that complements the spectral response characteristics of the solid state image pick-up device used. The device includes a rotating color filter disc interposed between the subject and a source of light, and can be arranged to adjust the amount of light of each of the three primary colors irradiated on the subject by initially selecting the respective areas of each color filter for transmitting each color and/or by sequentially adjusting the intensity of the light source in synchronism with each of the color filter areas passing before it and the synchronizing signals are generated by openings formed in light shielding regions of the disc.

5 Claims, 8 Drawing Figures

ILLUMINATING AND SYNCHRONIZING DEVICE FOR COLOR IMAGING EQUIPMENT

FIELD OF THE INVENTION

This invention relates to an illuminating device, for color imaging equipment such as a television camera, electronic camera, or endoscope which uses a solid state pickup device, to serve as an ideal illuminating means to irradiate light on a subject to complement the spectral response characteristics of the solid state image pickup device.

Recently, there has been a great increase in use of solid state devices as color image pickups in television cameras, electronic cameras, and other devices such as endoscopes. One color imaging method using a solid state image pickup device is arranged to illuminate the subject with a white light source and provides a color mosaic filter on the light receiving surface of the solid state image pick-up device to receive the light from the subject. Light received by the pickup device through the color mosaic filter generates imaging signals corresponding to the colors, which are then processed and displayed in color.

Another method is to provide an illuminating means that sequentially irradiates light of the three primary colors to illuminate the subject. The light from the subject is received directly by the solid state image pick-up device. The imaging signals are read in synchronism with the frame cycle for each color and are processed to display the image in color.

In the latter method, the spectral response characteristic, i.e., the luminous efficiency of the solid state image pick-up device for light of different colors, must be taken into consideration when designing the illuminating means used to sequentially irradiate light of the three primary colors on the subject.

The spectral luminous efficiency of a solid state image pick-up device is the ratio of the signal output of the CCD (charge coupled device) to the light intensity on it when the luminous intensity of the different wavelengths of light forming the illuminating light is the same. The spectral luminous efficiency of a CCD is very low in the blue color light region with a central wave length of 450 nm and increases in the direction of the green and red regions as shown in FIG. 1. Such a drop of sensitivity in the blue region is not limited to CCD devices, and is the same with MOS (Metal Oxide Semiconductor) type imaging devices using photo diodes. Therefore, when the solid state image pick-up device is used as an imaging means, a substantially ideal illuminating means is an illuminating source having a spectral luminous characteristic as shown in FIG. 2. That is, it is necessary to have a characteristic such that the intensity is the highest in the blue region and the intensity in the green (central wave length 540 nm) and red (central wave length 600 nm) regions decreases toward the infrared region, as shown in FIG. 2. If a light source having such spectral luminous intensity is used, the output of the imaging signals of the subject images corresponding to the blue, green and red colors will be obtained approximately at the same level and a proper white balance can be obtained on the display.

As a means for providing the light effect equivalent to the illuminating light source having such spectral luminous intensity as shown in FIG. 2, a device using a three-color decomposing rotary filter is proposed. The rotary filter, as shown in FIG. 3, is a color decomposing filter to decompose the light from a light source to illuminate a subject, or the light from a subject, into three colors sequentially, and has R (red), G (green) and B (blue) color filters each having a different area and arranged on a disc. When the disc is rotated at a constant speed and the color filters of different areas are irradiated by a light, the quantity of B light, G light and R light transmitted depends upon the areas of the B, G, and R filters, respectively, as long as the illuminating lamp used as the illuminating source provides a constant quantity of illuminating light and has ordinary spectral characteristics.

This method keeps the electrical signals of each color output from the solid state image pick-up device at a proper level by maximizing the B light and reducing the quantity of transmitted light in the sequence of G light and R light by selecting a proper area for each color filter of the rotary filter. Such a device can adjust the white balance of the picture image of the subject imaged and displayed.

In using this method to achieve the white balance by means of a rotary filter with different areas as shown in FIG. 3, the area ratios of the color filters are fixed. When this method is used to provide an illuminating means for an endoscope, it presents a problem that deviations may be caused in the white balance depending on the type of imaging means that is used with the illuminating means or because the light guide fiber bundle used to introduce the illuminating light to the subject is yellowed with age, thus resulting in a change of optical characteristics. Such white balance deviations cannot be corrected if the area ratio of each color filter is fixed.

OBJECT AND SUMMARY OF THE INVENTION

The object of the present invention is to provide an illuminating device for a color imaging device which can adjust the white balance to compensate for the spectral deterioration of the light guide fiber and for the spectral luminous efficiency of the type of imaging means that is used with the illuminating means, such as a solid state image pickup.

The apparatus of this invention is arranged to adjust the quantity of each color of light to an optimum value by rotating a filter, consisting of three color filters having the same or different areas and separated by a fixed light shielding space, at a constant speed in front of an illuminating light source, detecting the passage of each color filter area with a color detecting means provided near the rotary filter, having a signal generating means generate signals of different amplitude corresponding to the desired intensity of light of each color on the basis of the detected signal, driving a current control means in accordance with the amplitude of the signals, and changing the amount of current to the light source for each color to change the light intensity.

DETAILED DESCRIPTION OF THE PREFERRED EMBODIMENTS

Figure 1:
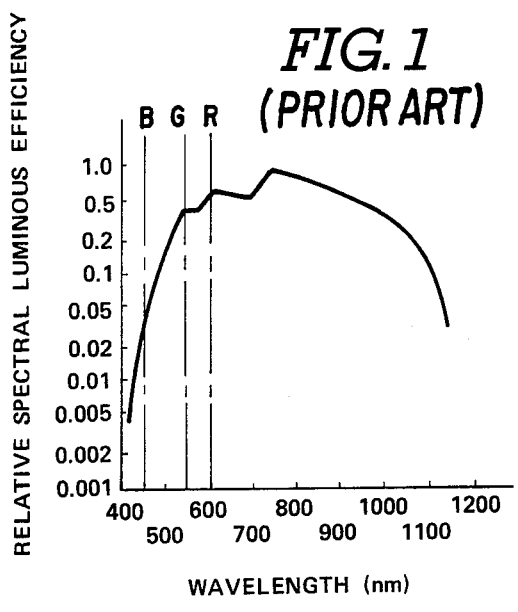
FIG. 1 is a graph showing the spectral luminous efficiency of a CCD.
Figure 3:
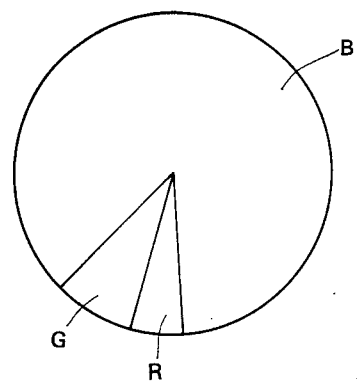
FIG. 3 is a front view showing the configuration of a rotary filter used for the illuminating device.
Figure 2:
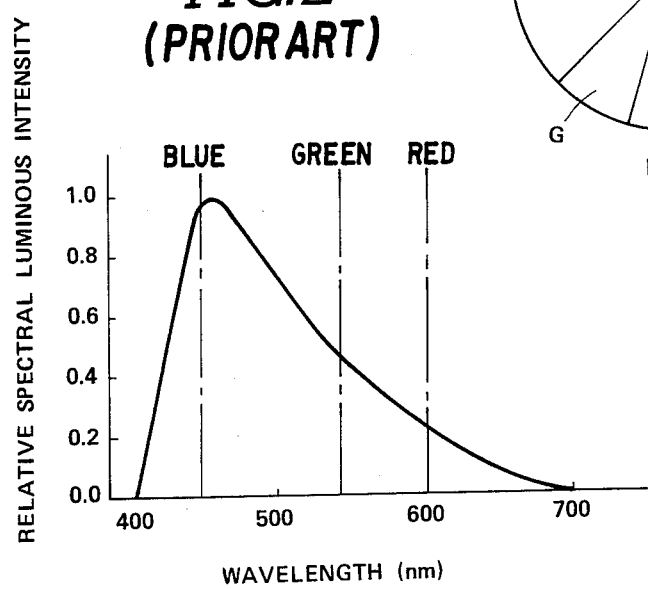
FIG. 2 is a graph showing the spectral luminous intensity of a substantially ideal light source for illuminating such a CCD.
Figure 4:
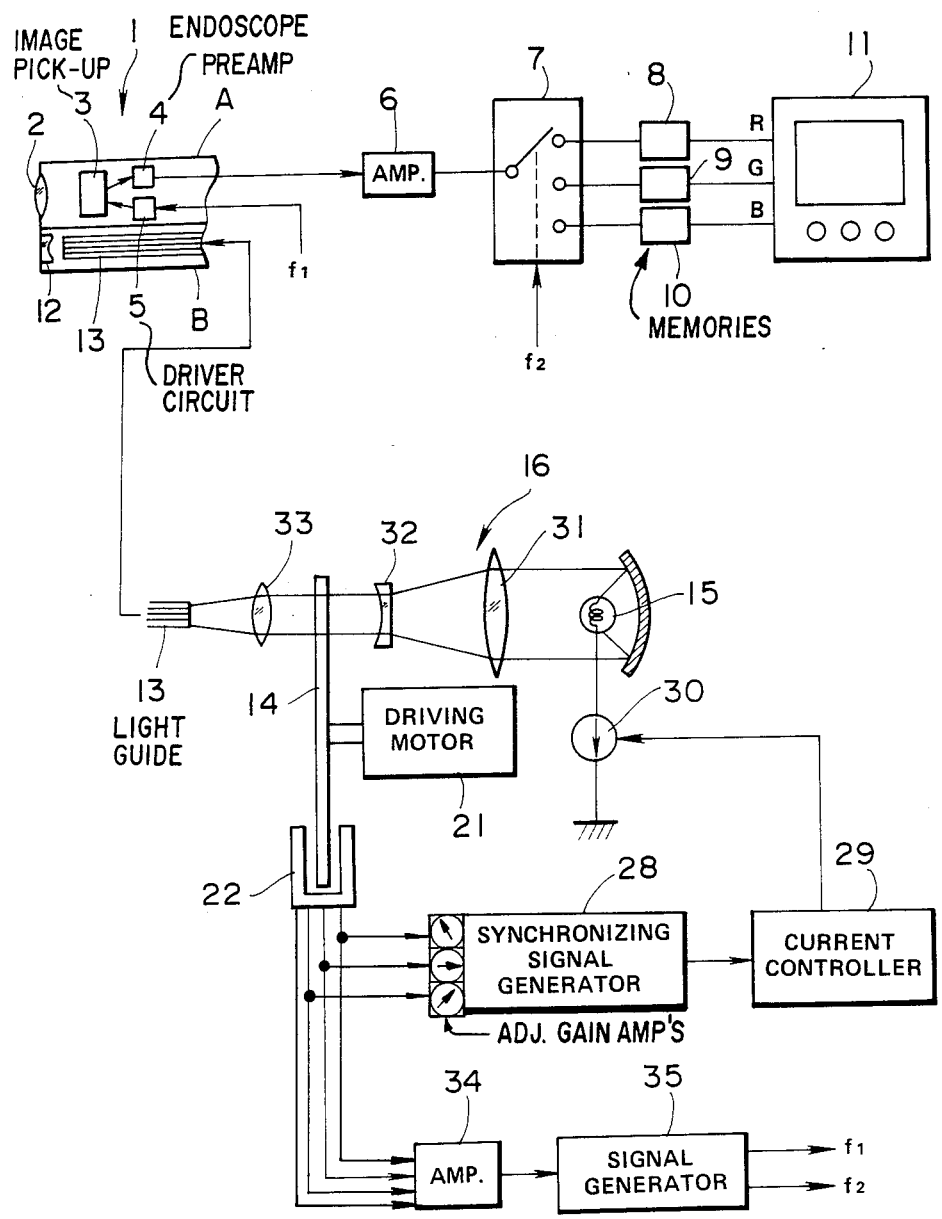
FIG. 4 is a block diagram showing an embodiment of the illuminating device of the present invention.

FIG. 4 shows the configuration of the illuminating device of the present invention. This embodiment shows one example of the application of the invention to an endoscope. Reference numeral 1 indicates the front end part of an endoscope which has an imaging side A and an illuminating side B. On the imaging side an imaging lens 2 is arranged to received light irradiated from a subject, and behind it a solid state image pick-up device 3 is positioned. The solid state image pick-up device 3 consists of an imaging area where a two-dimensional array of photodiodes is arranged to form the picture elements, a charge accumulating area and a scanning circuit.

The solid state image pick-up device 3 receives a light image of a subject, makes it into picture image signals and accumulates them, and the accumulated signals are read by a driver circuit 5 to which the reading clock signal f1 is input, and the signals are amplified and output by a preamplifier 4. The signals are further amplified by an amplifier 6, input to a switching circuit 7 in which they are selected for each frame using the frame switching signal f2 in accordance with each color of light, accumulated in the following frame memories 8, 9 and 10, read simultaneously from the memories 8, 9 and 10, and displayed in color by a color monitor 11.

On the illuminating side B of the front part 1 of the endoscope are an illuminating lens 12 to irradiate the illuminating light to a subject and behind it a light guide fiber 13 to introduce the light from an illuminating device to be described later. The light guide fiber 13 is extended to the rear of the endoscope where its end face receives illuminating light. The illuminating light is supplied by an illuminating device 16 which consists of three-color decomposing rotary filter 14 and a light source lamp 15, the current to which can be changed.

Figure 5:
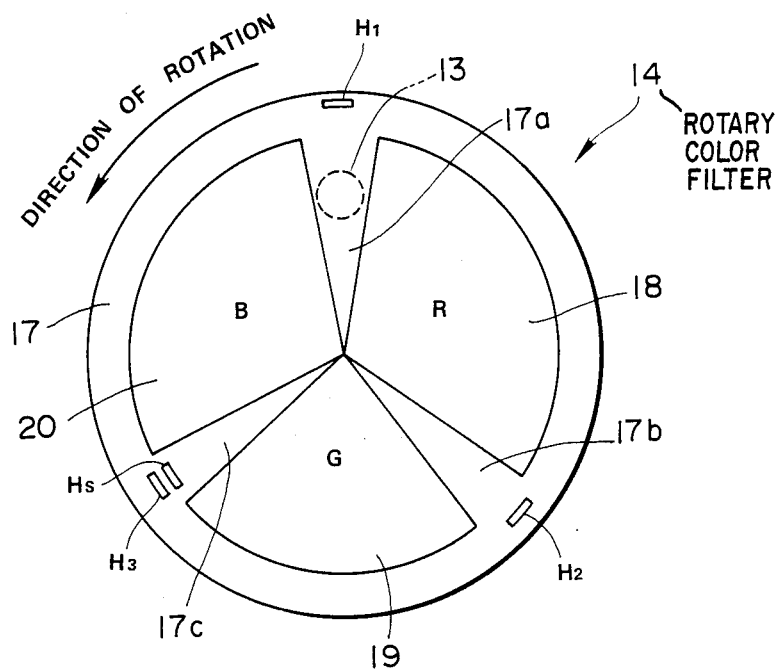
FIG. 5 is a front view showing an example of a preferred configuration of the rotary filter.

The rotary filter 14 used for the illuminating device 16 is formed as shown in FIG. 5. The rotary filter 14 consists of fan-shaped R, G and B light transmitting filters 18, 19 and 20, each of which may have a different area (or central angle) arranged in a circular light shielding frame body 17. For example, the area of the R filter 18 may be made big and that of the G filter 19 may be made small. In this case, the R, G and B filters 18, 19 and 20 are separated from one another by light shielding regions 17a, 17b and 17c of substantially the same area. Near the outer peripheral edge of the light shielding frame body 17, hole $H_1$ for R detection, hole $H_2$ for G detection and hole $H_3$ for B detection are provided. These holes $H_1$, $H_2$ and $H_3$ are provided at the positions corresponding to the light shielding region 17a, 17b and 17c, respectively, and are displaced from each other by approximately equal intervals in the radial direction. That is, the holes $H_1$, $H_2$, and $H_3$, in that order, are located progressively nearer to the center of the circle, hole $H_1$ being the greater distance from the center. In the light shielding region, e.g. 17c of the light shielding frame body 17, a start pulse detecting hole Hs, to detect each rotation of the rotary filter 14, is provided at a fourth position nearer to the center. The rotary filter 14 formed as above is rotated at a constant speed by a driving motor 21 as shown in FIG. 4.

Figure 6:
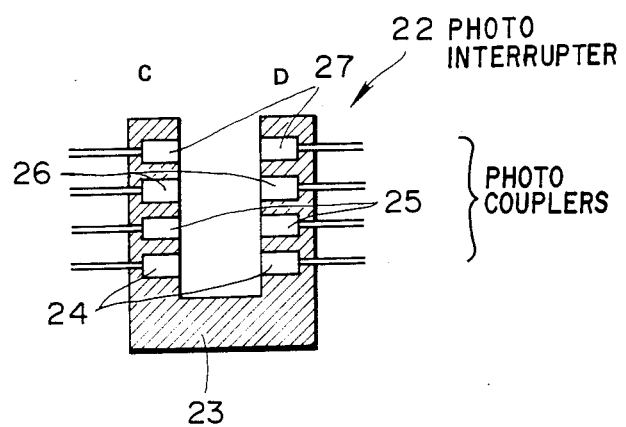
FIG. 6 is a sectional view showing an example of the configuration of the photo interrupter in FIG. 4.

The R, G and B detecting holes $H_1$, $H_2$, and $H_3$ and the start pulse detecting hole Hs of the aforementioned rotary filter 14 can be detected by a photo interrupter 22 provided near the outer peripheral edge of the rotary filter 14. The photo interrupter 22 consists of, for example, four pairs of photo couplers as shown in FIG. 6. That is, the photo interrupter 22 consists of a U-shaped frame body 23 having a plurality of light emitting elements in a light emitting element column C and a plurality of light receiving elements in a light receiving element column D, each pair of light emitting and receiving elements facing each other to provide four sets of photo couplers 24, 25, 26 and 27. Of these photo couplers, the photo coupler 24 detects the R detecting hole $H_1$ of the rotary filter 14, the photo coupler 25 detects the G detecting hole $H_2$, the photo coupler 26 detect the B detecting hole $H_3$ and the photo coupler 27 detects the start pulse detecting hole Hs. The photo couplers 24, 25, 26 and 27 are operated by a power source (not illustrated).

Every time the photo interrupter 22 detects the R, G or B detecting holes $H_1$, $H_2$ or $H_3$, a color frame detecting signal is output from the corresponding coupler and input to a synchronizing signal generator 28 (FIG. 4). The synchronizing signal generator 28 consists of, e.g. 3 amplifiers each with a different gain (or preferably three amplifiers so formed that the gain can be adjusted), and it generates pulses with a different amplitude for each color R, G or B, in synchronism with the light shielding regions 17a, 17b or 17c by inputting the color frame detecting signals to each amplifier. The pulses of different preset amplitudes for each color R, G or B that are output from the synchronizing signal generator 28 are input to a current controller 29. The current controller 29 produces a control voltage that is proportional to the pulse amplitude at the time of each such pulse input and maintains that voltage value until the subsequent pulse is received. That is, the current controller 29 outputs the control voltage in steps of different amplitude during the R lighting period, the B lighting period, and the G lighting period, and applies it to the control terminal of a variable current source 30. The variable current source 30 supplies the current to the light source lamp 15 equipped with a reflecting mirror, and its current value is controlled in accordance with the control voltage. Therefore, the quantity or intensity of light irradiated by the light source lamp 15 is changed in accordance with the amplitude of the control voltage, and the light is irradiated to the rotary filter 14 in parallel rays through the lenses 31 and 32.

This means that the quantity or intensity of irradiated light is switched in synchronism with the color filters 18, 19 and 20 of the rotary filter 14. The light transmitted through the rotary filter 14 is condensed by the lens 33 to be incident on the end face of the light guide fiber 13. The R, G and B color frame detecting pulse signals of holes $H_1$, $H_2$ and $H_3$ and the start pulse signal of the hole Hs detected by the photo interrupter 22 are amplified by an amplifier 34 and supplied to a signal generator 35. The signal generator 35 generates the color frame switching signal f2 on the basis of the R, G, and B color frame detecting pulse signals and the start pulse signal, and at the same time generates the reading clock signal f1 using an internal oscillator. The reading clock signal f1 is output during the light interrupting period of the rotary filter 14 so that the signal of the solid state image pick-up device 3 can be read within that period.

Figure 7:
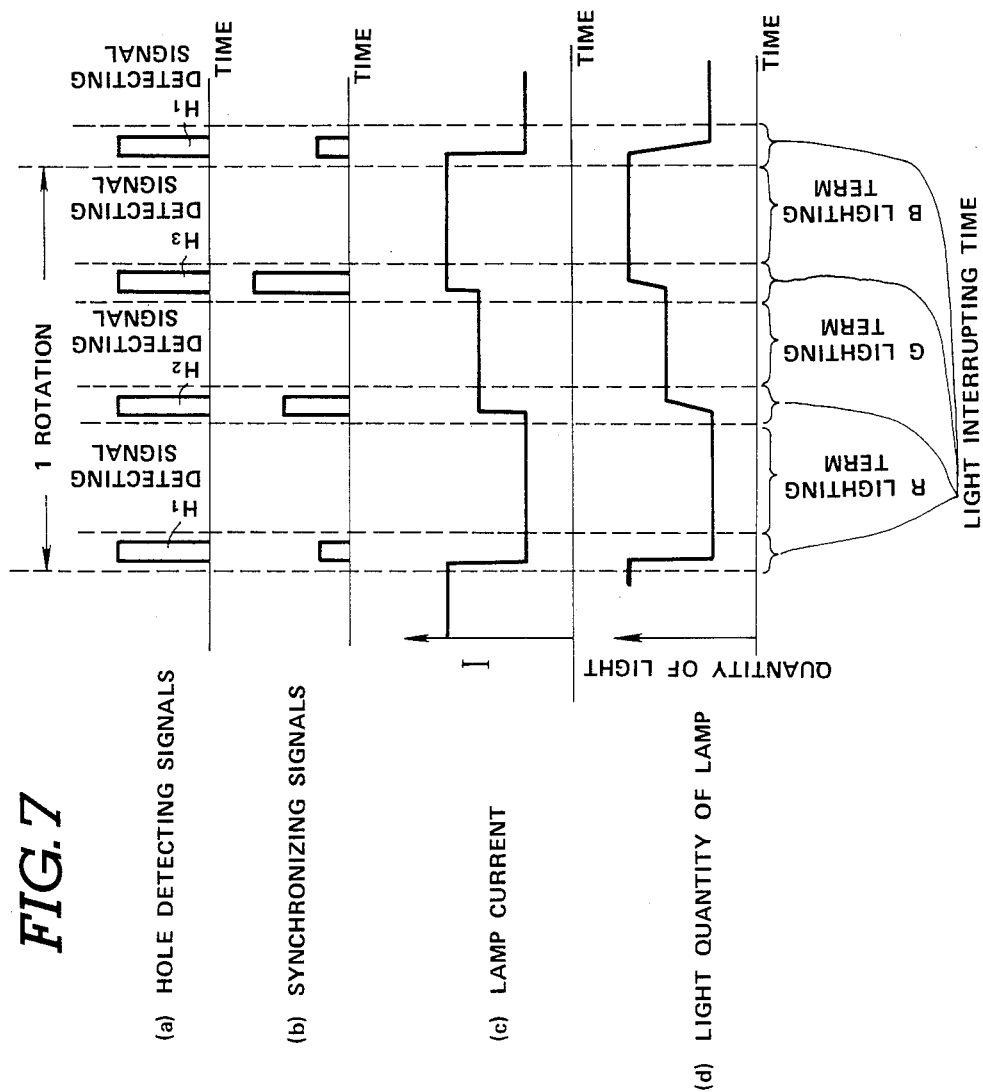
FIG. 7 is an explanatory drawing explaining the operation of the device in FIG. 4.

The operation of the illuminating device 16 formed as described above will be explained referring to FIG. 7. Firstly, when the rotary filter 14 is being rotated at a constant speed, the photo interrupter 22 detects the R, G and B detecting holes $H_1$, $H_2$, and $H_3$ at different time intervals depending upon the spacing of regions 17a, 17b, and 17c, and outputs color frame detecting pulse signals all with the same amplitude as shown in (a) of FIG. 7. For these pulse signals, for example, the period of time from the $H_1$ detection to $H_2$ may be long and the period of time from $H_2$ detection to $H_3$ detection may be short, depending on the R, G or B filter period. Then the R, G and B color frame detecting signals are input to the synchronizing signal generator 28 in which the input/output amplitude ratio is set differently for R, G and B. By setting the input/output amplitude ratio of the synchronizing signal generator 28 at maximum for B and at smaller values for G and R, the signal output will be pulse signals of such relationship in amplitude as shown in (b). The synchronizing signals are input to the current controller 29 to produce the control voltage (not illustrated) to control the lamp current source 30. The control voltage is a step voltage which changes in accordance with the synchronizing signal amplitude, and by this the lamp current I is changed in steps as shown in (c) of FIG. 7. Therefore, the quantity of light irradiated by the light source lamp 15 is also changed substantially in accordance with the current I as shown in (d). As a result, if the area ratio (or ratio of central angle) of the R, G and B filters 18, 19 and 20 arranged on the rotary filter 14 is determined and the values of the three synchronizing signals output by the synchronizing signal generator 28 are set properly in accordance with the detection of the holes $H_1$, $H_2$ and $H_3$, it is possible to obtain an illuminating light with optimum spectral luminous intensity to compensate for the spectral luminous efficiency of the solid state image pick-up device 3. That is, the quantity or intensity of light of the three primary colors can be controlled to have an optimum value by adjusting both the area ratio (or ratio of central angle) of the color filters and the amount of electrical current.

Figure 8:
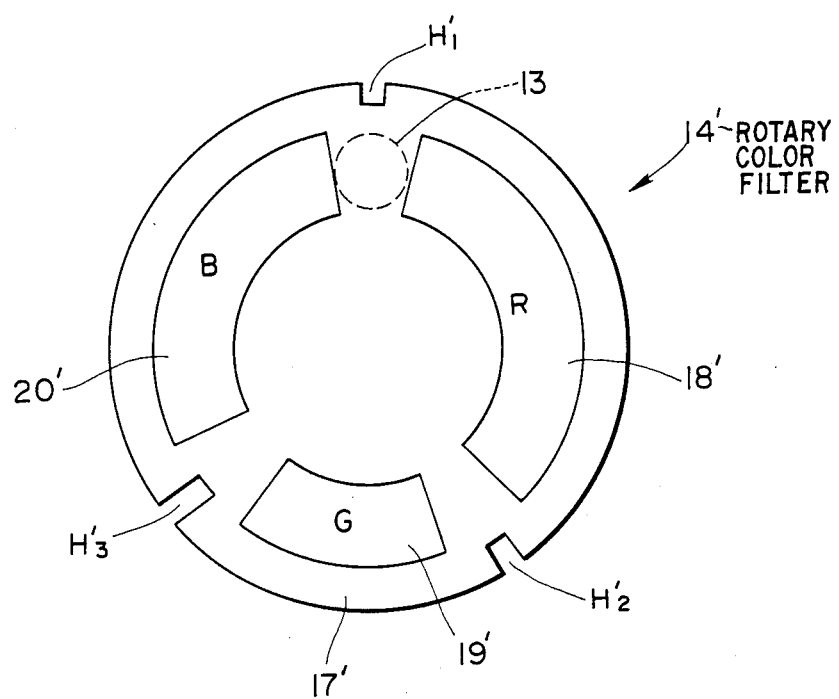
FIG. 8 shows another embodiment of the rotary filter.

Although FIG. 5 shows the R, G and B detecting holes $H_1$, $H_2$, and $H_3$ formed on the light shielding frame body 17, slits can be formed instead of holes by cutting slits in the outer peripheral edge of the light shielding frame body 17, as shown in FIG. 8. In such a case, the radial depths of the slits may be made larger in the sequence of R, G and B so that the R, G and B can be detected by a photo interrupter 22 as that in FIG. 6. When the slits formed as described above are detected by the photo interrupter 22 shown in FIG. 6, the R detecting slit $H'_1$ is detected by the photo coupler 24 only, the G detecting slit $H'_2$ is detected by two photo couplers 24 and 25 and the B detecting slit $H'_3$ is detected by three photo couplers 24, 25 and 26 because the R, G and B detecting slits are different in depth from one another. For this reason, if the combined output of the photo couplers is obtained every time the R, G or B is detected, the photo interrupter 22 output will provide detecting signals having different levels like the synchronizing signals as shown in (b) of FIG. 7. Therefore, when the hole is replaced by the slit, it is also possible to use the output of the photo interrupter 22 as the synchronizing signal after amplifying and shaping to produce a step-like control voltage for input to the current controller 29.

Also, FIG. 5 shows the fan-like R, G and B color filters 18, 19 and 20, but they need not necessarily be fan-shaped. That is, so long as the area of each color filter portion that passes the end face of the light guide fiber 13, i.e. the effective area, remains the same the shape of the filters may be arcuate as shown in FIG. 8, or of another shape.

The area ratios of the R, G and B color filters 18, 19 and 20 is not limited to the illustrated examples of FIGS. 5 and 8, and should be set as required in accordance with the characteristics of the type of the imaging device to be used and the condition of the light guide fiber.

According to the present invention as described above, the illuminating light is irradiated from a light source whose current can be changed onto a rotary filter consisting of three color filters having different areas and divided from one another by light shielding regions of approximately the same size, and the light source current can be arbitrarily controlled for each color filter region. Therefore, the intensity of light of each of the three colors can be controlled to provide optimum values through either selecting the areas of the three color filter regions or the electrical adjustment of the lamp current, or both, and it is possible to obtain a combined illumination that can compensate for the spectral luminous efficiency of any type of solid state image pick-up device used as a color imaging means. Therefore, if the aforementioned illuminating device is used in combination with, for example, the imaging device of an endoscope, the level of light output received by the imaging means can be finely adjusted among the three primary colors in accordance with the spectral deterioration of the light guide fiber and the type and condition of the imaging means, and the balance of the three colors necessary to provide a proper white balance can be adjusted extremely accurately.

It is clear that various embodiments of a wide range can be formed on the basis of this invention without departing from the spirit and scope of the invention. Accordingly, the invention is not restricted by the particular embodiments described herein except to the extent recited in the accompanying claims.

We claim:

1. An illuminating and synchronizing system for lighting a subject of an electronic color imaging device which includes a solid state iamge pick-up device, comprising:
   an illuminating light source;
   color filter means for decomposing light from said light source into different colors comprising a rotating disc having a plurality of color filter areas of different colors separated from one another by light shielding regions and disposed to pass in the light path of said light source between said light source and said subject;
   first timing means for producing a color frame detecting signal for each said color filter area to denote the times of passage of said color filter areas in the light path of said light source;
   synchronizing signal generating means, responsive to said color frame detecting signals, including three adjustable gain amplifiers and being synchronized by said first timing means to generate a synchronizing signal having a different amplitude corresponding to each of said color filter areas, respectively, and current controlling means connected to said synchronizing signal generating means and to said light source to control the amount of current to said light source, sequentially, in response to said synchronizing signal of different ampitudes and in proportion to amplitudes of the synchronizing signal for sequentially controlling the amount of light passing through said color filter areas in synchronism with the time of passage of respective color filter areas in the light path of said light source;

second timing means for producing a start signal to indicate the beginning of each rotation of said rotating disc;

said first and second timing means comprising openings formed in peripheral areas of said disc light shielding regions, and photo-interrupter means including a plurality of photo-couplers for producing output signals which indicate passage of said openings through said photo-interrupter means; and signal generator means arranged to receive the output signals of said first and second timing means, and connected to said electronic color imaging device, for generating first reading clock signals to synchronize a driver circuit of said color imaging device to read a signal form said solid state image pick-up device during passage of light shielding regions of said disc between said light source and said subject, and for generating second timing signals to serve as color frame switching signals of said color imaging device.

2. A system as recited in claim 1 wherein said signal generating means comprises a plurality of adjustable gain amplifiers, each responsive to a color frame detecting signal for a respective color filter area arranged to provide a synchronizing signal having a preadjusted amplitude for each color filter area, respectively.

3. An illuminating and synchronizing system as recited in claim 1, wherein said openings formed in said light shielding regions consist of detecting holes corresponding to said color filter areas, a hole being positioned at a different radius of said disc for each color filter area.

4. A system as recited in claim 1, wherein said openings formed in said light shielding regions consist of slits of different radial depths formed in a peripheral area of said disc.

5. A system as recited in claim 4, wherein said color frame detecting signals produced therein each have an amplitude determined by the radial depth of said slits, respectively, and the amount of light passing through each of said color filter areas is controlled in accordance with the amplitude of said color frame detecting signals.

* * * * *